United States Patent [19]

Gervasutti

[11] Patent Number: 5,093,523

[45] Date of Patent: Mar. 3, 1992

[54] PROCESS FOR THE PREPARATION OF PERFLUOROSUCCINYLFLUORIDE

[75] Inventor: Claudio Gervasutti, Venezia, Italy

[73] Assignee: Ausimont S.r.L., Milan, Italy

[21] Appl. No.: 515,088

[22] Filed: Apr. 26, 1990

[30] Foreign Application Priority Data

Apr. 27, 1989 [IT] Italy ................... 20294 A/89

[51] Int. Cl.⁵ ........................... C07C 51/305
[52] U.S. Cl. ..................... 562/850; 562/851
[58] Field of Search ............ 562/843, 840, 888, 849, 562/850, 851, 852

[56] References Cited

U.S. PATENT DOCUMENTS 3,102,139  8/1963  Lawlor et al. ............ 562/888
3,160,659 12/1964  Dittman et al. .
3,725,475  4/1973  Paucksch et al. .
3,899,531  8/1975  Siegemund .
4,116,977  9/1978  Yamabe et al. ............ 549/266

OTHER PUBLICATIONS

Patent Abstracts of Japan, vol. 6, No. 110, 22 Jun. 1982, JP-A-5740434 (Asahi Class).
Patent Abstracts of Japan, vol. 8, No. 138, 27 Jun. 1984, JP-A-5948436 (Daikin Kogyo).

*Primary Examiner*—Marianne Cintins
*Assistant Examiner*—Margaret Argo
*Attorney, Agent, or Firm*—Stevens, Davis, Miller & Mosher

[57] ABSTRACT

A perfluorosuccinylfluoride is prepared by the reaction of a gaseous mixture of 1,4-dibromoperfluorobutane with $SO_3$ in oleum with at least 65% of free $SO_3$ containing a catalyst comprising, besides mono- and bivalent mercury sulphates, $B_2O_3$ in quantities of from 0.3% to 8% by weight with respect to the free $SO_3$ present in the "oleum" during course of the reaction.

4 Claims, No Drawings

PROCESS FOR THE PREPARATION OF PERFLUOROSUCCINYLFLUORIDE

DESCRIPTION OF THE INVENTION

The present invention concerns a process for the preparation of perfluorosuccinylfluoride (COF—CF$_2$—CF$_2$—COF). The perfluorosuccinylfluoride is a known product used amongst others as an intermediate in the preparation of fluoro derivatives. Methods for its preparation consist, for instance, in the electro-chemical fluorination of succinylfluoride acid, in the oxidation of perfluorocyclobutene, or in the oxidation of 1,4-diiodineperfluorocyclobutane.

All these processes give very low yields of perfluorosuccinylfluoride and, thus, are not suited for being use on an industrial scale.

According to British Patent No. 2082570, perfluorosuccinylfluoride is prepared according to a method which foresees the dimerization and subsequent de-halogenation of a difluoroacetylfluoride of the formula: XCF$_2$COF($\underline{X}$=Cl, Br or I) with yields of about 50%.

Said method of preparation shows, however, the drawback of requiring very critical operational parameters, such as, for instance, the anhydrousness of the raw reaction material, the use of metals and high reaction temperatures, which if not strictly respected result in considerable drops in the yield. Moreover, the starting difluoroacetylfluoride turns out to be difficult to prepare and this further complicates said process.

It is known from U.S. Pat. No. 3,102,139 to obtain fluoroalkanoyl-monohalides by oxidation carried out with SO$_3$ stabilized with boric anhydride, in the absence of free acids and in the presence of mercurous and mercuric sulphates, of fluoroalkanes of the formula RCXYZ, wherein $\underline{R}$ is perhalogenated alkyl radical with F and/or Cl atoms; $\underline{X}$=H, Br, Cl and F and Y and Z are respectively Cl, Br or I.

According to the quoted patent, from the possibility of obtaining fluoroalkanoyl halides are excluded the fluoroalkanes in which the reactive terminal or end carbon atom contains two fluorine atoms, and more particularly fluoroalkanes in which both the terminal or end carbon atoms are monobromo-difluorinates such as for instance in 1,4-dibromo-perfluorobutane (BrF$_2$C—CF$_2$—CF$_2$—CF$_2$Br).

It is also known from Japanese Pat. Appl. Nr. 5948436 to prepare perfluoroalkylenecarboxylic difluoride acids by the oxidation of α,ω-diiodoperfluoroalkanes by means of SO$_3$ or oleum, in the presence of a catalyst consisting of phosphorus, molybdenum and tin, or of compounds thereof.

Said preparation has, however, the drawback of requiring the use of iodurated perfluoroalkanes which are not easily available as industrial products and thus have, to be especially prepared.

Lastly, it is known from U.S. Pat. No. 4,116,977 to carry out the oxidation of α,ω-diiodoperfluoroalkanes with oleum at 30%–70% of SO$_3$ in the presence of catalysts consisting of mercury sulphate.

According to such a reaction, only fluoroalkanes containing more than 6 carbon atoms will allow the obtention of high-yields of fluorides of perfluoro acids, while those with from 3 to 5 carbon atoms, such as α,ω-diiodoperfluorobutane, will give yields in fluorides of perfluoro acids of only 10–15%.

It has now been found by the Applicant that it is possible to prepare, also operating by a continuous process, perfluorosuccinylfluoride with high yields and conversions, starting from 1,4-dibromo-perfluorobutane by carrying out the oxidation by means of sulphuric anhydride in the presence of a catalyst consisting of a mixture of mono- and bi-valent mercury sulphates and boric anhydride.

More particularly, it is possible to carry out such preparation by reacting mixtures of sulphuric anhydride with 1,4-dibromo-perfluorobutane in an oleum containing at least 65% by weight of free sulphuric anhydride, and in which there are dissolved the components of the catalyst.

The reaction temperature, which corresponds to that of the catalyst-containing oleum, is between 45° and 70° C., but preferably is between 50° and 55° C.

Practically, one operates feeding a mixture of 1,4-dibromoperfluorobutane and sulphuric anhydride into an oleum containing at least 65% by weight of free sulphuric anhydride. The quantity of boric anhydride in the oleum may be between 0.3 and 8% by weight, but preferably between 2.5 and 5.5% by weight based on the total weight of the free sulphuric anhydride present in the oleum during the course of the reaction.

The quantity of mercury and mercurous sulphates in the oleum vary, each of which being, between 0.5% and 5% b.w. with respect to the weight of free sulphuric anhydride present during the reaction. Preferably one operates with weight ratios of B$_2$O$_3$/HgSO$_4$/Hg$_2$SO$_4$ of about 10/1/1.

Thus, an object of the present invention is to provide a process for the preparation of perfluorosuccinylfluoride, which process consists in reacting a mixture of 1,4-dibromo-perfluorobutane with sulphuric anhydride in oleum, in a quantity of at least 65% b.w., in the presence of catalysts consisting of mercury sulphates and boric anhydride in quantities between 0.3 and 8% by weight with respect to the weight of free sulphuric anhydride.

Preferably, the quantity of free sulphuric anhydride in oleum during the reaction is between 65% and 80% by weight. The mixture of sulphuric anhydride and 1,4-dibromo-perfluorobutane, which is made to react with the oleum, shows molar ratios of SO$_3$/1,4-dibromoperfluorine greater than 1, but preferably between 2 and 3.

During the course of the reaction there is formed perfluorosuccinylfluoride together with free bromine and sulphurous anhydride. The bromine may be removed by reaction with cyclohexanone and the formation of bromocyclohexane, while the sulphurous anhydride is eliminated by reaction with potassium fluoride dissolved in distilled and anhydrous glycolmethylenic dimethylether (DIGLIMA).

The following example is given for purely illustrative purposes and does not in any way limit the scope of the inventive idea of this invention.

EXAMPLE

Into a 500 cc reactor, fitted with a stirrer and a condenser, there were introduced 50 cc of oleum at 65% of free sulphuric anhydride, 5 g of B$_2$O$_3$, 0.5 g of Hg$_2$SO$_4$ and 0.5 grams of HgSO$_4$.

The oleum in the reactor was then brought up to a temperature of 50°–55° C. by immersing the reactor into a Galden bath (perfluoropolyether) kept at a temperature of 90° C. and then, under stirring, into the oleum, by means of a metering cylinder, there was fed in a mixture of sulphuric anhydride and 1,4-dibromo-perfluorobutane in a by-weight ratio of 115:260, the feeding being carried out for about one hour until reaching a total weight of 375 grams of such a mixture.

The above mixture had been obtained by distilling sulphuric anhydride from an oleum with 65% of free sulphuric anhydride, by heating at not more than 130° C., then condensing and gathering the sulphuric anhydride thus obtained in a bottle containing 135 g of 1,4-dibromo-perfluorobutane, and then feeding into the reactor the mixture of the two components.

During the reaction, under operational conditions, the temperature in the condenser was maintained at −5° C.

The reaction products that flow out of the head of the condenser were conveyed through an adsorption set consisting of potassium fluoride in diglime, then through the rinsing system with cyclohexene to a condensation trap maintained at −60° C. by an ethylalcohol/dry ice mixture. Under such conditions there was obtained about 120 grams of raw reaction product at 85% by weight of perfluorosuccinylfluoride from which, by distillation, there was obtained 70 g of perfluorosuccinylfluoride at a 99% titre, with a yield of about 50%.

What is claimed is:

1. A process for the preparation of perfluorosuccinylfluoride, consisting of reacting a mixture of 1,4-dibromoperfluorobutane with free sulphuric anhydride in oleum in the presence of a catalyst,
   wherein the oleum contains at least 65% by weight of the free sulphuric anhydride, and the catalyst consists of mercury, mercurous sulphates and boric anhydride, the boric anhydride being present in an amount between 0.3 and 8% by weight of the free sulphuric anhydride during the course of the reaction.

2. The process according to claim 1, wherein the amount of free sulphuric anhydride is between 65% and 80% by weight.

3. The process according to claim 1, wherein the by-weight ratio of $B_2O_3/HgSO_4/Hg_2SO_4$ is about 10:1:1.

4. The process according to claim 1, wherein any sulphurous anhydride formed during the reaction is adsorbed by a potassium fluoride solution in glycol-dimethylenic dimethylether.

* * * * *